(12) United States Patent
Nagaike et al.

(10) Patent No.: US 8,480,952 B2
(45) Date of Patent: Jul. 9, 2013

(54) METHOD OF MANUFACTURING PHARMACEUTICAL PREPARATIONS CONTAINING LIPOSOMES

(75) Inventors: Chiaki Nagaike, Asaka (JP); Yasuyuki Motokui, Hachioji (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 1784 days.

(21) Appl. No.: 11/187,397

(22) Filed: Jul. 22, 2005

(65) Prior Publication Data

US 2006/0034907 A1 Feb. 16, 2006

(30) Foreign Application Priority Data

Aug. 11, 2004 (JP) ................................. 2004-234583
Aug. 31, 2004 (JP) ................................. 2004-252931
Sep. 8, 2004 (JP) ................................. 2004-261585

(51) Int. Cl.
*A61K 9/127* (2006.01)
*A61K 47/34* (2006.01)

(52) U.S. Cl.
USPC ............ 420/450; 424/450; 424/45; 424/9.51; 264/4.1; 264/4.3; 425/5

(58) Field of Classification Search
USPC ........... 424/450, 45, 9.51; 264/4.1, 4.6; 425/5
See application file for complete search history.

(56) References Cited

U.S. PATENT DOCUMENTS

| | | | | |
|---|---|---|---|---|
| 4,192,859 A | * | 3/1980 | Mackaness et al. | 424/9.45 |
| 5,094,854 A | * | 3/1992 | Ogawa et al. | 424/423 |
| 5,277,914 A | * | 1/1994 | Szoka, Jr. | 424/450 |
| 5,326,552 A | * | 7/1994 | Na et al. | 424/9.455 |
| 5,508,060 A | * | 4/1996 | Perman et al. | 427/2.14 |
| 5,554,382 A | * | 9/1996 | Castor | 424/450 |
| 5,700,482 A | * | 12/1997 | Frederiksen et al. | 424/450 |
| 6,270,806 B1 | * | 8/2001 | Liversidge et al. | 424/497 |
| 2004/0099976 A1 | * | 5/2004 | Otake et al. | 264/4.1 |
| 2005/0084453 A1 | * | 4/2005 | Ueda et al. | 424/9.45 |

FOREIGN PATENT DOCUMENTS

| | | |
|---|---|---|
| CN | 1451372 A | 10/2003 |
| EP | 0 616 801 A1 | 9/1994 |
| EP | 1 334 765 A1 | 8/2003 |
| EP | 1 679 084 A1 | 7/2006 |
| JP | 2003-119120 A | 4/2003 |
| JP | 2005-170928 A | 6/2005 |
| WO | WO 88/09165 | * 12/1988 |
| WO | WO 96/15774 A1 | 5/1996 |
| WO | WO 02/32564 A1 | 4/2002 |
| WO | WO 2005/037325 A1 | 4/2005 |

OTHER PUBLICATIONS

Otake et al, Development of a new preparation method of liposomes using supercritical carbon dioxide, Langmuir 2001, vol. 17, 3898-3901.*
Genz et al. The influence of cholesterol on the main phase transition of unilamellar dipalmytoylphosphatidylcholine vesicles, Biophysics Journal, vol. 50, 1986, 1043-1051.*
Moribe et al. Encapsulation charecteristics of nystatin in liposomes: effect of cholesterol and polyethylene glycol derivatives, International journal of pharmaceutics, 188 (1999) 193-202.*
Extended European Search Report (EESR) dated May 18, 2012 (in English) in counterpart European Application No. 05766258.7.
Abe M. et al.: Database WPI Thomson Scientific, London, GB: "Manufacture of liposome, useful as skin external preparation, involves mixing membrane lipids containing phosphatide and/or glycolipid with carbon dioxide in threshold or subcritical state in indispensable condition": Apr. 23, 2003: XP55026833. (In English).
Kawakatsu S. et al.: Database WPI Thomson Scientific, London, GB: "Radiographic contrast medium useful as non-oral contrast medium for radiography, e.g. X-ray diagnosis, comprises liposome that comprising vesicles including water-soluble nonionic iodine compound": Jun. 30, 2005: XP55026840. (In English).
Lu F. et al.: Database WPI Thomson Scientific, London, GB: "Method for preparing medicine targeted liposome includes providing SOD, dissolving SOD to obtain solution, magnetizing, preparing water-in-oil emulsion, supercritical fluid swelling precipitation, and freeze drying": Oct. 29, 2003: XP55026846. (In English).
Frederikson L. et al.: "Preparation of Liposomes Encapsulating Water-Soluble Compounds Using Supercritical Carbon Dioxide": Journal of Pharmaceutical Sciences: vol. 86, No. 8: Aug. 1, 1997: pp. 921-928: XP002591244. (In English).

* cited by examiner

*Primary Examiner* — Savitha Rao
(74) *Attorney, Agent, or Firm* — Holtz Holtz Goodman & Chick PC

(57) ABSTRACT

A method of manufacturing liposome-containing preparations which contain liposomes exhibiting superior stability in vivo and high enclosure rate of a drug is disclosed, comprising mixing a supercritical or subcritical carbon dioxide, one or more liposome membrane constituents including a phospholipid exhibiting a phase transition temperature and a water-soluble chemical.

11 Claims, No Drawings

METHOD OF MANUFACTURING PHARMACEUTICAL PREPARATIONS CONTAINING LIPOSOMES

This application claims priority from Japanese Patent Application Nos. JP2004-234583 filed on Aug. 11, 2004; JP2004-252931 filed on Aug. 31, 2004; and JP2004-261585 filed on Sep. 8, 2004 which are incorporated hereinto by reference.

FIELD OF THE INVENTION

The present invention relates to a method of manufacturing liposome-containing pharmaceutical preparations which contain liposome exhibiting superior stability in vivo and high enclosure rate of a drug, and liposome-containing pharmaceutical preparations obtained thereby.

BACKGROUND OF THE INVENTION

Liposomes are closed vesicles of bimolecular layer (liposomal membrane) formed mainly of phospholipid and having a structure and functions similar to living membrane, which have been employed as various pharmaceutical materials. Liposomes can construct a so-called capsule structure in which water-soluble chemical substances are included in the internal aqueous phase and oil-soluble chemical substances are retained in the interior of the bimolecular layer and have been employed in various fields such as medical diagnosis, medical treatments and cosmetics. Recently, active studies have been made studies of application to a drug delivery system (DDS).

Hitherto, there has been employed the Bangham method or the reverse phase vaporization method (also denoted as the REV method) to prepare drug-enclosing liposomes. In these methods, drugs are enclosed within liposomes exhibiting high safety as raw materials and appropriate degradability in vivo, whereas it is necessary to use organic solvents as a solvent for phospholipid forming the liposomal membrane in the process of preparing liposomes. However, the thus obtained liposome-containing pharmaceutical preparation results in problems that an unremoved organic solvent remains in the preparation, exerting a toxic effect upon the living body.

Further, conventional methods are difficult to allow a sufficient amount of drugs to be enclosed in the liposomes so that problems arise which necessitate dosing of relatively large amounts of the liposome-containing pharmaceutical preparation, imposing an excessive burden on the patient. Taking into account application to contrast medium for diagnosis of which dose becomes large, compared to drugs for medical treatments, there has been desired a liposome-containing pharmaceutical preparation exhibiting high retention efficiency (enclosure ratio) of contrast medium material.

JP-A No. 2003-119120 (hereinafter, the term JP-A refers to Japanese Patent Application Publication) discloses a method of manufacturing liposomes enclosing water-soluble electrolytic chemicals, using supercritical carbon dioxide. This method which is feasible to set various manufacturing conditions can achieve enhanced enclosure of water-soluble chemicals more easily than the conventional method of manufacturing a liposome suspension. However, the use of supercritical carbon dioxide, as disclosed in the foregoing patent document enables preparation of liposomes having enhanced enclosure of water-soluble chemicals, compared to the conventional methods but still further enhancement of the enclosure ratio has been desired.

When liposomes applied to the uses including diagnosis and medical treatments are unstable in vivo, the liposomal membrane is ruptured and enclosed chemicals are effused in an early stage. As a result, there occurred problems that the chemicals were not delivered to the intended site and it was difficult to control sustained-release as one of the functions of the liposome. Accordingly, liposomes exhibiting superior stability in vivo have been desired.

To solve the foregoing problems, there has been disclosed a method of allowing a buffer solution exhibiting a pH of 9.5 or less at 15° C. and containing ammonia or a water-soluble amine to be included in the liposome dispersion to enhance stability of the liposome, as described in published Japanese translation of PCT international publication for patent applications. However, even liposomes obtained by such a method still had a problem with respect to stability in vivo.

SUMMARY OF THE INVENTION

Accordingly, it is an object of the present invention to provide a method of preparing liposome-containing pharmaceutical preparations which contain liposomes exhibiting superior stability in vivo and high enclosure rate of drugs and liposome-containing pharmaceutical preparations.

In one aspect the invention is directed to a method of manufacturing a liposome-containing preparation comprising mixing a supercritical or subcritical carbon dioxide, one or more liposome membrane constituents including a phospholipid exhibiting a phase transition temperature and a water-soluble chemical.

Preferred embodiments of the invention are disclosed in the dependent claims.

The phase transition temperature of the phospholipid is preferably within the range of 22° to 60° C. The foregoing supercritical or subcritical carbon dioxide, the liposome membrane constituting material and the drug are preferably mixed, while stirring strongly, leading to enhanced enclosure of the drug in the liposomes.

A phospholipid exhibiting the foregoing phase transition temperature is selected preferable from the group of dimyristoylphosphatidylcholine, dipalmitoylphosphatidylcholine, hydrogenated soybean lecithin, hydrogenated soybean phosphatidylcholine and distearoylphosphatidylcholine, and dimyristoylphosphatidylcholine and/or dipalmitoylphosphatidylcholine are specifically preferred.

The drug is preferably a contrast medium material or an anticancer substance.

DETAILED DESCRIPTION OF THE INVENTION

The manufacturing method of liposomes relating to the invention is a method comprising a process of mixing at least a phospholipid (preferably exhibiting a phase transition temperature) as a liposome membrane constituent and a pharmaceutical chemicals with supercritical or subcritical carbon dioxide (hereinafter, also denoted simply as a supercritical carbon dioxide) to form liposomes.

Liposome Membrane Constituent

In general, a phospholipid and/or a glycolipid are preferably used as a constituent of a lipid membrane (or lipid bilayer) of the liposome, in which a phospholipid exhibiting a phase transition temperature is contained.

Specific examples of phospholipids include phosphatidylcholine, phosphatidylserine, phosphatidylethanolamine, phosphatidylglycerol, phosphatidylinositol, phosphatidic acid, cardiolipin and sphingomyelin. There are also usable phospholipids derived from plants and animals such as egg yolk or soybean and their hydrogenation products or hydroxide derivatives, so-called semi-synthetic phospholipids. Fatty acids constituting a phospholipid are not specifically limited, and saturated and unsaturated fatty acids are usable.

Specific examples of neutral phospholipid include dipalmitoylphosphatidylcholine (DPPC), distearoylphosphatidylcholine (DSPC), dimyristoylphosphatidylcholine (DMPC), dioleylphosphatidylcholine (DOPC), dimyristoylphosphatidylethanolamine, dipalmitolphosphatidylethanolamine, and distearoylphosphatidylethanolamine.

In addition to the foregoing neutral phospholipid, there may be include charged phospholipid such as an anionic phospholipid and cationic phospholipid, polymerizable phospholipid and cationic (positive-charged) lipid. Examples of negative-charged phospholipid include dipalmitoylphosphatidylglycerol (DPPG), dimyristoylphosphatidylglycerol, distearoylphosphatidylserine (DSPS), distearoylphosphatidylserine (DSPS), dipalmotoylphosphatidylinositol (DPPI), distearoylphosphatidylinositol (DSPI), distearoyl-phosphatidic acid (DSPA), dipalmitoylphospatidic acid (DPPA) and dimyristoylphospatidic acid.

Examples of cationic phospholipid include an eater of phosphatidic acid and aminoalcohol, such as an ester of dipalmotoylphosphatidic acid (DPPA) or distearoylphosphatidic acid, and hydroxyethylenediamine.

Phospholipids used in the invention include at least a phospholipid exhibiting a phase transition temperature. The phase transition temperature of phospholipid refers to a temperature at which phase transition between both states of gel and liquid crystal of the phospholipid is caused. The phase transition temperature can be determined by differential thermal analysis using a differential thermal calorimeter. The phase transition temperature of a phospholipid is preferably from 22 to 60° C., more preferably from 30 to 60° C., and still more preferably from 40 to 55 oc.

Examples of a phospholipid exhibiting a phase transition temperature include dimyristoylphosphatidylcholine (phase transition temperature: 23-24° C.), dipalmitoylphosphatidylcholine (41.0-41.5° C.), hydrogenated soybean lecithin (53° C.), hydrogenated phosphatidylcholine (54° C.), and distearoylphosphatidylcholine (54.1-58.0° C.). Of these, dimyristoylphosphatidylcholine and dipalmitoylphosphatidylcholine are preferred and dipalmitoylphosphatidylcholine is more preferred. In the invention, one or more of these are used.

The phospholipid exhibiting a phase transition temperature preferably accounts for 40% to 100%, and more preferably 50% to 80% by weight of the total amount of phospholipid. Using a phospholipid in an amount described above, liposomes exhibiting superior stability in vivo can be prepared at a mixing temperature described later.

Phospholipids include at least one phospholipid exhibiting a phase transition temperature and one or more other phospholipids may be used. In cases where two or more charged phospholipids are used, preferably, they are all positive-charged or negative-charged ones in terms of prevention of coagulation of liposomes.

Examples of cationic lipids usable in the invention include 1,2-dioleoyloxy-3-(trimethylammonium)propane (DOTAP), N,N-dioctadecylamidoglycylspermine (DOGS), dimethyloctadecylammonium bromide (DDAB), N-[1-(2,3-dioleyloxy)propyl]-N,N,N-trimethylammonium chloride (DOTMA), 2,3-dioleyloxy-N-[2(spermine-carboxamido) ethyl]-N,N-dimethyl-1-propaneaminiumtrifluoroacetate (DOSPA) and N-[1-(2,3-dimyristyloxy)propyl]-N,N-dimethyl-N-(2-hydroxyethyl)ammonium bromide (DMRIE).

Examples of glyceroglycolipids include glycerolipids such as digalactosyldiglyceride and digalactosyldiglyceride sulfuric acid ester; sphingoglycolipids such as galactosylceramide, galactosylceramide sulfuric acid ester, lactosylceramide, ganglioside G7, ganglioside G6 and ganglioside G4.

In addition to the foregoing lipids, other substances may optionally incorporated as a constituent of the liposome membrane. For example, cholesterol, dihydrocholesterol, cholesterol ester, phytosterol, sitosterol, stigmasterol, campesterol, cholestanol, and lanosterol are cited as a layer stabilizer. Further, sterol derivatives such as 1-O-sterolglucoside, 1-O-sterolmaltoside and 1-O-sterolgalactoside have been shown to be effective in stabilization of liposome (as described in JP-A No. 5-245357) and of the foregoing sterols, cholesterol is specifically preferred. Sterols are used usually in an amount of from 0.05 to 1.5 parts by weight, preferably from 0.2 to 1 parts by weight and more preferably from 0.3 to 0.8 parts by weight per part by weight of phospholipid. An amount of less than 0.05 parts by weight does not achieve stabilization by a sterol to enhance dispersibility of mixed lipids, and an amount of more than 2 parts by weight inhibits liposome formation or results in unstable formation thereof.

A cholesterol enclosed in the liposome membrane is capable of functioning as an anchor to introduce a polyalkylene oxide. JP-A No. 9-3093 discloses novel cholesterol derivatives, in which various functional substances can be efficiently fixed at the top of a polyoxyalkylene chain, which can be employed as a liposome constituent.

In addition to the foregoing sterols, glycols may be added as a constituent of a liposome vesicular membrane. Examples of glycols include ethylene glycol, diethylene glycol, triethylene glycol, propylene glycol, dipropylene glycol, trimethylene glycol, and 1,4-butanediol. Glycols are used preferably in an amount of 0.01% to 20% by weight of the total weight of lipids, and more preferably 0.5% to 10% by weight.

It is preferred to use, as a constituent of liposome membrane, a compound containing a polyethylene glycol group (also denoted as PEG group), more preferably, a phospholipid or cholesterol containing a polyethylene glycol group. A phospholipid to be derived is optimally chosen from the foregoing phospholipids. In the compound containing a polyethylene glycol group, appropriate change of the number of an oxyethylene unit of the PEG groups, that is represented by —(CH$^2$CH$_2$O)$_n$—H, can control functions of the compound. A PEG group having oxyethylene units of 10 to 3500 (more preferably 100 to 2000) is preferred. Polyethylene glycol is used preferably in an amount of 0.1% to 30%, and more preferably 1% to 15% by weight of lipid constituting liposomes. The compound containing a polyethylene glycol group can be prepared by the method described in JP-A No. 7-165770.

The use of liposomes using such a compound containing a polyethylene glycol group as a dissolution aid in supercritical carbon dioxide can prepare liposomes having a relatively high enclosure ratio, without using an organic solvent.

Pharmaceutical Chemicals

Pharmaceutical chemicals used in the invention are those which are enclosed in the interior of a lipid vesicular membrane or within the inner water phase and specific examples thereof include a contrast medium, an anticancer material, an antifungal material, an antioxidant material, an antibacterial material, an anti-inflammatory material, a circulation-promoting material, a skin-whitening material, rough skin-preventing material, an aging prevention material, a new hair growth promotion material, a moisturizing material, a hormone drug, vitamins, dyes and proteins.

Water-soluble chemicals are dissolved in a prescribed amount of aqueous medium by commonly known methods and used as an aqueous solution. The concentration of a water-soluble chemical is optimally chosen depending on solubility and manufacturing conditions of the water-soluble chemical. Examples of an aqueous medium include not only distilled water, water for injection and pure water, but also physiological saline solution, various kinds of buffer solutions and aqueous solutions containing salts.

Liposome-containing preparations of the invention preferably employs a contrast medium material or an anticancer material as a water-soluble chemical.

Water-soluble iodine compounds are usable as a contrast medium material. Any ionic or nonionic water-soluble iodine compound capable of functioning as a contrast medium is usable in the inventions. Nonionic iodine compounds, which generally exhibit a lower osmotic pressure than ionic iodine compounds, are preferred. Specifically, water-soluble nonionic iodine compounds containing at least one iodophenyl group such as a 2,4,6-triiodophenyl group are preferred in the invention.

Specific examples of such a nonionic iodine compound include iopamidol, iomeprol, iohexol, iopentol, iopromide, ioxilane, iosimide, ioversol, iotrolan, iotasul, iodixanol, iodecimol, and 1,3-bis-[N-3,5-bis-(2,3-dihydroxypropylaminocarbonyl)-2,4,6-triiodophenyl]-N-hydroxyacetyl-amio]-propane. These compounds may be used singly or in combination thereof.

As iodine compounds suitable for radiographic contrast medium of this invention are preferred iomeprol, iopamidol, iotrolan and iodixanol, which exhibit high hydrophilicity and a low osmotic pressure even at relatively high concentration. These non-electrolytic materials can be enclosed within liposomes by the supercritical carbon dioxide method.

The concentration of the water-soluble iodine compound contained in the contrast medium can be arbitrarily set based on factors such as properties of the contrast medium compound, the intended dosage route of a medicine and clinical guidelines. The quantity of the water-soluble iodine compound enclosed in liposomes is typically 5% to 40% by weight, preferably 5% to 35% and more preferably 10% to 25% by weight, based on total iodine compounds contained in the contrast medium. This enclosure ratio is below the limit of the closed-packed structure of liposome particles so that retention stability of contrast medium material in the liposomes is not vitiated.

Examples of an anticancer compound include methotrexate, doxorubicin, ebirubicin, daunoruvicin, vincristine, vinblastine, etoposide, erypsitine, captodecin, pacritaxecel, docetaxecel, cisplatin and prednisone. These compounds may be use alone or in combination thereof.

The above-cited compounds include not only their free forms but also their salts and hydrates.

Hereinafter, there will be described the method of manufacturing liposome-containing preparations of the invention.

In one preferred embodiment of the invention, the manufacturing method of liposome-containing preparations comprises:

mixing one or more liposome membrane constituents including at least a phospholipid exhibiting a phase transition temperature and liquefied carbon dioxide, and optionally a lipophilic chemical in a pressure vessel, while stirring (step 1), subsequently, increasing the pressure within the pressure vessel with heating at a temperature of 32 to 55° C. to bring the carbon dioxide to the supercritical or subcritical state (step 2), supplying an aqueous solution of a water-soluble chemical to the mixture of the liposome membrane constituents and supercritical carbon dioxide with stirring to form a mixed solution (step 3), and decreasing the pressure within the vessel to discharge the carbon dioxide from the mixed solution to form an aqueous dispersion of liposomes enclosing the water-soluble chemical (step 4).

Preferably, the method further comprises subjecting the aqueous dispersion of liposomes to filtration using a filter membrane having a pore size of 0.1 to 1.0 μm, preferably 0.1 to 0.45 μm (step 5).

The foregoing respective steps will be further described below.

Step 1:

In the step 1, one or more liposome membrane constituents including at least a phospholipid exhibiting a phase transition temperature, liquefied carbon dioxide, and optionally one or more lipophilic chemicals are mixed in a pressure vessel with stirring. The addition order thereof is not specifically limited and stirring conditions are not specifically limited so long as mixing is achieved.

The pressure vessel is preferably a stainless steel autoclave having pressure resistance up to 500 atm. and provided with a glass window to visually observe the interior.

Amounts of the liposome membrane constituents are optimally determined in accordance with the kind of chemicals and the production scale. Amounts of lipophilic chemicals are also optimally determined in accordance with the activity of the lipophilic chemicals and the enclosure ratio of the liposomes.

In the respective steps, the interior of the pressure vessel, the chemicals to be added to the pressure vessel, liquefied carbon dioxide and gases are controlled preferably under aseptic conditions and when supplied into the pressure vessel, it is preferred to conduct sterilization using a filtration means or the like.

Step 2:

In the step 2, the interior of the pressure vessel is heated at 32 to 55° C. and the pressure within the vessel is increased to bring liquefied carbon dioxide to the supercritical state. In the invention, the supercritical state is also inclusive of the subcritical state.

The temperature of supercritical carbon dioxide used in the invention is preferably from 32 to 55° C., more preferably 32 to 50° C., and till more preferably from 35 to 50° C. The optimum pressure of supercritical carbon dioxide, which is selected from the foregoing temperature range, is preferably from 50 to 500 $kg/cm^2$ and more preferably fro 100 to 400 $kg/cm^2$.

Since carbon dioxide is brought to the supercritical state at a temperature close to body temperature to form liposomes from a phospholipid, this liposome forming temperature is approximately equal to the temperature (body temperature) to which the liposomes, dosed as a pharmaceutical preparation, are subjected to in vivo. Accordingly, it is assumed that after the liposome preparation is dosed into a body, even if the liposomes are heated in vivo by the body temperature, such a temperature is approximately equal to the liposome forming temperature so that the arrangement of a phospholipid is barely influenced by the temperature, resulting in enhanced stability of liposomes in vivo.

The said effect is further pronounced by setting the temperature of supercritical carbon dioxide at a temperature of not more than a temperature of the phase transition temperature plus 10° C., more preferably not more than a temperature of the phase transition temperature plus 5° C., and still more preferably not more than the phase transition temperature. Hitherto, heating to a temperature of the phase transition temperature of a phospholipid plus ca. 20° C. brings a phospholipid having a phase transition temperature to the liquid crystal state, whereby fluidity is enhanced and the phospholipid is efficiently mixed with the supercritical carbon dioxide, facilitating liposome preparation. However, it was discovered by the inventors that when the temperature of supercritical carbon dioxide is brought to the phase transition temperature of the phospholipid or a lower temperature, the phospholipid is not excessively heated causing no denaturation and resulting in a regular arrangement of phospholipids to form liposome membrane. The thus obtained liposomes result in a stable membrane structure, making it easier to control sustained release property of liposomes and enhanced stability in vivo enables to stable chemical delivery to the intended site.

Step 3:

In the step 3, while the liposome membrane constituents and supercritical carbon dioxide are mixed with stirring by a prescribed stirring means, an aqueous solution of a water-soluble chemical is supplied thereto to prepare a mixed solution. The foregoing stirring is preferably subjected to strong agitation.

The strong agitation, the preferred range of which differs depending on the volume of the mixed solution and stirring means, means that, for example, a 10 to 100 ml solution is stirred using a nearly cylindrical stirring rod of 15 mm length and 5 mm diameter and a magnetic stirrer at a rate of 400 to 4,000 rpm (preferably 1,000 to 1,500 rpm). Even if the volume of the mixed solution or stirring means differ from the foregoing, it is preferred to set appropriate stirring conditions taking into account a shearing force which is given to the solution under the foregoing stirring conditions. Specifically, stirring conditions preferably satisfy the following requirement:

$$C = N \times V^{-0.15}$$

where C is the number of revolutions (rpm), V is the volume (L), of the mixed solution and N is 300 to 3,000. The strong agitation time is usually from 1 to 120 min., and preferably from 5 to 60 min. The foregoing strong agitation time includes the time for supplying the aqueous solution of chemicals.

Mixing liposome membrane constituents and supercritical carbon dioxide over a prescribed period of time by strong agitation under the foregoing conditions enhances liposome formation rate and obtain preparations containing liposomes exhibiting enhanced enclosure ratio of chemicals. Thus, strong agitation under such conditions promotes formation of liposomes and enhances the enclosure ratio of chemicals (or the proportion of enclosed chemicals).

Accordingly, it is specifically preferred to bring carbon dioxide to the supercritical state or subcritical state at the afore-mentioned temperature and mix the supercritical carbon dioxide and liposome membrane constituents under strong agitation over a given duration, whereby a pharmaceutical preparation containing liposomes exhibiting superior stability in vivo and an enhanced enclosure ratio of chemicals can be obtained. It is further to be noted that maintaining the supercritical state over a further extended time to continue strong agitation tends to enhance enclosure of chemicals within the liposomes.

It is preferred to apply ultrasonics when mixing supercritical carbon dioxide and liposome membrane constituents under the strong agitation condition. Application of ultrasonics allows liposome membrane constituents (lipids) to be dispersed as fine particles in supercritical carbon dioxide, whereby a liposome-containing preparation achieving enhanced formation of liposomes and exhibiting an enhanced enclosure rate of chemicals can be obtained.

Hitherto, the manufacturing method of liposome-containing preparations, according to the invention is described with respect to the process comprising: (1) mixing one or more liposome membrane constituents including at least a phospholipid exhibiting a phase transition temperature and liquefied carbon dioxide, and optionally a lipophilic chemical in a pressure vessel, while stirring; (2) subsequently, increasing the pressure within the pressure vessel with heating to bring the carbon dioxide to the supercritical or subcritical state; (3) supplying an aqueous solution of a water-soluble chemical to the mixture of the liposome membrane constituents and supercritical carbon dioxide with stirring to form a mixed solution An alternative method of manufacturing liposome-containing preparations of the invention, comprises: (1) one or more liposome membrane constituents and an aqueous solution of a water-soluble chemical, and optionally one or more lipophilic chemicals are mixed within a pressure vessel with stirring; (2) subsequently, liquefied carbon dioxide is supplied to the pressure vessel and increasing the temperature and pressure within the pressure vessel to bring the carbon dioxide to the supercritical state; (3) the liposome membrane constituents, the chemical and supercritical carbon dioxide are mixed with stirring to prepare a mixed solution. In this manufacturing method, it is not necessary to add a water-soluble chemical after formation of supercritical carbon dioxide, so that the temperature and pressure within the pressure vessel can be easily controlled, resulting in an enhanced liposome formation rate and enhanced enclosure of chemicals.

The liposome membrane constituents and the aqueous solution of a water-soluble chemical may be mixed after they are added to the pressure vessel, but in one preferred embodiment of the foregoing step (1), they are mixed in advance to prepare a suspension and then, the suspension is supplied to the pressure vessel. Preparing a suspension in advance makes it easier to supply the liposome membrane constituents and the aqueous solution of a water-soluble chemical into the pressure vessel, resulting in enhancement of the liposome formation rate and enclosure ratio of chemicals.

In another embodiment of the step (1), an aqueous solution of a water-soluble chemical and a dissolution aid, for example, a compound containing a polyethylene glycol group, as afore-mentioned, are mixed and then a liposome membrane constituents are further mixed to prepare a suspension. Dispersing a dissolution aid in the aqueous solution can dissolve the liposome membrane constituents in the aqueous solution, thereby resulting in the advantageous effects described above.

Further in another embodiment of the step (1), when liposome membrane constituents and an aqueous solution of a water-soluble chemical are mixed, or an aqueous solution of a water-soluble chemical and a dissolution aid are mixed and then liposome membrane constituents are mixed to prepare a suspension, ultrasonics are applied thereto to prepare a suspension and then, the prepared suspension is supplied into the pressure vessel.

Conditions for application of ultrasonics are appropriately chosen depending on the form, particle size distribution and enclosure ratio of liposomes, but it is desirable that ultrasonics of 10 to 100 kHz (preferably 15 to 45 kHz) is applied at 1 to 600 w/ml/min (preferably 5 to 500 w/ml/min). The applied amount of ultrasonics can be calculated from the rated output of an ultrasonic homogenizer to be used, the volume of suspension and the applying time.

Preparation of the suspension with applying ultrasonics under the foregoing conditions can disperse liposome membrane constituents (lipids) in the form of fine particles in an aqueous solution of a water-soluble chemical, and even in a manufacturing apparatus of production-scale, there can be achieved manufacture of a liposome-containing preparation exhibiting enhanced liposome formation and enclosure of chemicals. Such advantageous effects are assumed to be due to the fact that the arrangement of phospholipid is initiated while applying ultrasonics to the suspension, which promotes the subsequent formation of liposomes which are formed by mixing the suspension with supercritical carbon dioxide.

Liposome membrane constituents and an aqueous solution of a water-soluble chemical are mixed with applying ultrasonics, while heating preferably at a temperature within the range from the phase transition temperature of a phospholipid to a temperature of the phase transition temperature plus 50° C. (which does not exceed 100° C.). Heating at a temperature higher than the phase transition temperature bring a phospholipid exhibiting a phase transition temperature to the state of liquid crystal, leading to enhanced fluidity and facilitating the arrangement of the phospholipid, and thereby resulting in enhanced formation of liposomes and enclosure of chemicals.

Further, liquefied carbon dioxide is supplied to the pressure vessel including the thus obtained suspension.

Liquefied carbon dioxide can be manufactured by pressure-cooling gaseous carbon dioxide. The obtained liquefied carbon dioxide is supplied to the pressure vessel with maintaining the liquid state. The carbon dioxide may be added at one time or intermittently. The supplying amount of liquefied carbon dioxide is appropriately chosen depending on liposome membrane constituents, the kind of water-soluble chemical and the production scale.

Step 4

After liposome membrane constituents, supercritical carbon dioxide and an aqueous solution of a chemical are mixed in the foregoing step 3, in the step 4, the pressure within the pressure vessel is decreased and carbon dioxide is discharged from the mixture to prepare an aqueous dispersion containing liposomes enclosing the chemical.

In the step 3, the liposomes are assumed to be phase-inversed to a water-phase and decreasing the pressure within the system to discharge carbon dioxide forms an aqueous dispersion of liposomes enclosing a chemical. In the case of manufacturing a contrast medium, the chemical may be included in an aqueous phase other than in the interior of the liposomes. Since the aqueous solution is enclosed in the interior of the liposomes, a contrast medium material exists not only in the water phase outside the liposomes but also mainly in the water phase within the liposomes, which is in the state of so-called enclosure.

Step 5

In the step 5, the thus obtained aqueous liposome dispersion was filtered using a membrane filter having a pore size of 0.1 to 1.0 μm.

Specifically, when a negative pressure exists in the interior of the pressure vessel, a sterilized gas is supplied into the pressure vessel. Examples of such a gas include atmospheric air, carbon dioxide, nitrogen, helium and argon.

After the pressure within the pressure vessel is brought to atmospheric pressure by supplying such a gas, an aqueous dispersion of liposomes is filtered using a membrane filter having a pore size of 0.1 to 1.0 μm. Such filtering operation can readily adjust the particle size of liposomes, leading to a liposome-containing preparation exhibiting a uniform particle size. Filtration is conducted using, for example, a hydrostatic type extrusion apparatus provided with a filter having a pore size of 0.1 to 1.0 μm. Specifically, the liposome dispersion is forcibly passed through a filter, using various types of hydrostatic extrusion apparatuses, such as EXTRUDER (trade name, product by Nichiyu Liposome Co., Ltd.) or LIPONIZER (trade name, product by Nomura Microscience Co., Ltd.). There are optimally used various filters such as polycarbonate type or cellulose type. Extrusion filtration methods are described in, for example, Biochim. Biophys. Acta 557, 9 (1979).

Introduction of the extrusion operating step, in addition to sizing described above, results in advantages such as exchange of a liposome dispersion, removal of unwanted material and filtration sterilization. Prior to filtration with a membrane filter having the foregoing pore size, preliminary filtration may be conducted using a membrane filter of approximately 1.0 to 2.0 μm for the purpose of sizing or removal of unwanted material.

In the manufacture of liposome-containing preparations of the invention, an aqueous dispersion of liposomes can be refined by filtration using the membrane filters described above or optionally, by methods such as centrifugal separation, ultrafiltration or gel permeation to remove chemicals which have not been retained within the liposomes, or concentrated to a prescribed concentration. Further, the liposome dispersion may be mixed with auxiliary agents such as a diluting agent.

Liposome containing preparations of the invention may be obtained by subjecting the aqueous dispersion of liposomes to freeze-drying. The freeze-dried liposomes are used by dispersion in an aqueous medium immediately before use.

According to the manufacturing method of liposome-containing preparations of the invention, pharmaceutical chemicals can efficiently be enclosed within the liposomes and there can also be obtained a pharmaceutical preparation which includes liposomes exhibiting superior stability in vivo.

The thus manufactured liposome-containing preparation is comprised of liposomes enclosing pharmaceutical chemicals and the average particle size of the liposomes is usually from 0.05 to 2.0 μm, preferably from 0.05 to 1.0 μm, and more preferably from 0.05 to 0.5 μm. The average particle size is appropriately set in accordance with the object such as medical treatments, medical diagnosis, or radiography. To achieve selective delivery to the tumor site, for example, the liposome particle size is preferably from 0.10 to 0.20 μm, and more preferably from 0.11 to 0.13 μm, whereby a medically effective material or a contrast medium can be selectively concentrated to cancer tissue. Pores on the vascularized wall of solid cancerous tissue are abnormally larger than the 30 to 80 nm pores of the capillary wall fenestra of normal tissue, so that even a large molecule of ca. 0.1 to ca. 0.2 μm leaks through the vascular wall. Therefore, liposomes having the foregoing size can be concentrated selectively into the cancer tissue. This is known as the EPR effect, which is due to permeability of the vascularized wall of cancerous tissue which is higher than the microvascular wall of normal tissue.

The liposome particle size can be determined in such a manner that a dispersion containing liposomes enclosing pharmaceutical chemicals is frozen and fractured, following which carbon is vapor-deposited onto the fractured interfaces and the deposited carbon is observed with an electron microscope (freeze fracture TEM method). The central vesicle size refers to a liposome particle size having the highest frequencies in the liposome particle size distribution.

The thus obtained liposome is one which is comprised substantially of a single membrane or a few membranes. The liposome of a single membrane is a liposome which is comprised of unilamellar vesicles, that is, a unilamellar vesicle formed of a single phospholipid bilayer. The liposome comprised substantially of a single membrane means that vesicles are each made up of a phospholipid bilayer, the replica of which is recognized nearly as a single layer in transmission electron microscopic (TEM) observation using a freeze-fracture replica technique. Thus, when observing the imprint of particles remaining in the carbon film, one having no difference in level is judged as a unilamellar vesicle. The foregoing expression, substantially means that such unilamellar vesicles are contained preferably in an amount of at least 80%, and more preferably at least 90%, based on the total liposome amount, i.e., the total amount of vesicles contained in the radiographic contrast medium.

The single membrane liposome or liposome comprised of a few membranes, that is, unilamellar vesicles can be efficiently prepared using the foregoing supercritical carbon dioxide as a solvent for lipids and by a phase separation method using water. Unilamellar vesicles have advantages such that the amount of added liposome or a given lipid amount is usually less than that of multilamellar vesicles. On the contrary, in conventional methods for preparation of liposome, a liposome comprised of multilamellar vesicles (MLV), that is, multilamellar vesicles often account for a fairly high proportion. Accordingly, operations such as exposure to ultrasonic or filtering through given-sized pores are required to raise the proportion of unilamellar liposome. However, manufacturing liposomes using supercritical carbon dioxide can efficiently form liposomes of unilamellar or several-lamellar vesicles, leading to enhanced enclosure of chemicals within the liposomes.

In cases when a pharmaceutical chemical such as a contrast medium or an anticancer compound is enclosed in the liposomes, in addition to the delivery efficiency and retention stability of an anticancer compound and the like, the amount of lipid membrane must be taken into account. The amount of a chemical enclosed in the liposome vesicles is preferably from 1 to 8, more preferably from 3 to 8, and still more preferably from 5 to 8, in terms of the weight ratio of the chemical included in the vesicles to the lipid forming the vesicular membrane.

A weight ratio of the chemical enclosed in the liposome vesicles of less than 1 necessitates injection of a relatively large amount of the lipid, resulting in lowered delivery efficiency of the chemical. Further, the viscosity of the preparation increases and power applied when injected is increased so that pain given to the patient also increases. On the contrary, when the weight ratio of the included iodine compound to the lipid of the liposome membrane exceeds 8, the liposome becomes structurally unstable and diffusion or leakage of the chemical from the liposome membrane is caused during storage or even after being injected into the organism.

The liposome-containing preparation of the invention can enclose various chemicals within the liposomes and the form of the preparation is determined taking into account working-effects and storage stability of the chemicals. When chemicals such as a contrast medium or an anticancer compound are enclosed in liposomes, the liposome-containing preparation is non-orally given to a person through intravascular dosage as injection or dripping.

The present invention will be further explained based on the following examples but is not limited thereto.

Example 1

A mixture of 300 mg of dipalmitoylphosphatidylcholine (DPPC, product by NIPPON OIL &FATS CO., LTD.) and 100 mg of PEG-phospholipid (SUNBRIGHT DSPE-020CN, lipid modified with polyethylene glycol, product by NIPPON OIL &FATS CO., LTD.) was added into a stainless steel autoclave and after 13 g of liquid carbon dioxide was added thereto, the interior of the vessel was made to a temperature of 50° C. and a pressure of 120 kg/cm$^2$ to bring the carbon dioxide to the supercritical state. While maintaining such a state, 10 g of an aqueous solution of Iohexol (iodine content: 240 mg/ml) was further added thereto and mixed with vigorously stirring over a period of 10 min. using a magnetic stirrer (a nearly cylindrical stirring rod of 15 mm length and 5 mm diameter) at a rate of 1000 rpm. Thereafter, the pressure within the pressure vessel was reduced to ca. 10 kg/cm$^2$ to discharge the carbon dioxide. Employing the pressure within the vessel, the dispersion was discharged from the vessel and recovered to obtain a liposome dispersion containing Iohexol. Further, the thus obtained dispersion was subjected to pressure filtration using a 0.45 μm cellulose type filter. After completion of filtration, the liposome dispersion was put into a vial and subjected to autoclave sterilization at 121° C. for 20 min. to obtain a liposome-containing preparation.

Measurement results of the enclosure ratio of chemicals, the average vesicular particle size and particle size distribution (which is the percentage of particles of 1 μm or more) are shown in Table 1.

Example 2

Into a stainless steel autoclave was added 900 mg of dipalmitoylphosphatidylcholine (DPPC, product by NIPPON OIL &FATS CO., LTD.), subsequently, 40 g of liquid carbon dioxide was added thereto, the interior of the vessel was made to a temperature of 40° C. and a pressure of 120 kg/cm$^2$ to bring the carbon dioxide to the supercritical state. While maintaining such a state, 40 g of an aqueous solution of Iopamidol (iodine content: 200 mg/ml) was further added thereto and mixed with vigorously stirring over a period of 20 min. using Three-One motor provided with 3 piece blade at a rate of 2000 rpm. Thereafter, the pressure within the pressure vessel was reduced to ca. 10 kg/cm$^2$ to discharge carbon dioxide. Employing the pressure within the vessel, a dispersion was discharged from the vessel and recovered to obtain a liposome dispersion containing Iopamidol. Further, the thus obtained dispersion was subjected to pressure filtration using a 0.45 μm cellulose type filter. After completion of filtration, the liposome dispersion was put into a vial and subjected to autoclave sterilization at 121° C. for 20 min. to obtain a liposome-containing preparation.

Measurement results of the enclosure ratio of chemical, the average vesicular particle size and particle size distribution (which is the percentage of particles of 1 μm or more) are shown in Table 1.

Example 3

A mixture of 300 mg of dimyristoylphosphatidylcholine (DMPC, product by NIPPON OIL &FATS CO., LTD.), 40 mg of cholesterol HP (product by NIPPON OIL &FATS CO., LTD.) and 50 mg of dipalmotoylphsphatudylglycerol (COATSOME MG-6060LS, product by NIPPON OIL &FATS CO., LTD.) as a glycerol lipid were added into a stainless steel autoclave and after 13 g of liquid carbon dioxide was added thereto, the interior of the vessel was made to a temperature of 48° C. and a pressure of 120 kg/cm$^2$ to bring the carbon dioxide to the supercritical state. While maintaining such a state, 10 g of an aqueous solution of Iohexol (iodine content: 200 mg/ml) was further added thereto and mixed with vigorously stirring over a period of 10 min. using a magnetic stirrer (a nearly cylindrical stirring rod of 3 mm length and 5 mm diameter) at a rate of 1200 rpm. Thereafter, the pressure within the pressure vessel was reduced to ca. 10 kg/cm$^2$ to discharge carbon dioxide. Employing the pressure within the vessel, a dispersion was discharged from the vessel and recovered to obtain a liposome dispersion containing Iohexol. Further, the thus obtained dispersion was subjected to pressure filtration using a 0.45 μm cellulose type filter. After completion of filtration, the liposome dispersion was put into a vial and subjected to autoclave sterilization at 121° C. for 20 min. to obtain a liposome-containing preparation.

Measurement results of the enclosure ratio of chemical, the average vesicular particle size and particle size distribution (which is the percentage of particles of 1 μm or more) are shown in Table 1.

Determination of Enclosure Ratio:

Liposome-containing preparations were each placed in a permeable membrane and dialysis was conducted three times in physiological saline, thereafter, liposomes was ruptured in a mixed solution of ethanol/water (3/1) and absorbance was measured using a spectrophotometer to determine the quantity of an iodine compound enclosed in liposomes and the enclosure ratio (%).

Determination of Particle Size

The average particle size (μm) and the particle size distribution which is the ratio (%) of particles of 1 mμ or more were determined using electrophoresis light scattering photometer (produced by Ohtsuka Denshi Co.).

TABLE 1

|  | Phospholipid (*1) | Temperature in Vessel (° C.) | Enclosure Ratio (%) | Average Particle Size (μm) | Particle Size Distribution (%) |
| --- | --- | --- | --- | --- | --- |
| Example 1 | DPPC (42) | 50 | 17 | 0.33 | <5*2 |
| Example 2 | DPPC (42) | 40 | 17 | 0.36 | 7 |
| Example 3 | DMPC (23) | 48 | 16 | 0.27 | <5 |

(*1) phase transition temperature (° C.)
*2less than 5

Example 4

Dipalmitoylphosphatidylcholine (DPPC) of 300 mg and 10 g of an aqueous solution of Iohexol (iodine content: 200 mg/ml) were mixed and dispersed over a period of 5 min. using a compact homogenizer (ULTRATALAX, trade name, produced by IKA Japan Corp.) at a rate of 6000 rpm to obtain a suspension. The suspension was added into a stainless steel pressure vessel, and after 13 g of liquefied carbon dioxide was added thereto, the interior of the vessel was made to a temperature of 60° C. and a pressure of 120 kg/cm$^2$ to bring the carbon dioxide to the supercritical state and such a state was further maintained for 10 min. Thereafter, the pressure within the pressure vessel was reduced to ca. 10 kg/cm$^2$ to discharge carbon dioxide. Employing the pressure within the vessel, a dispersion was discharged from the vessel and recovered to obtain a liposome dispersion containing Iohexol. Further, the thus obtained dispersion was subjected to pressure filtration using a 0.45 μm cellulose type filter. After completion of filtration, the liposome dispersion was put into a vial and subjected to autoclave sterilization at 121° C. for 20 min. to obtain a liposome-containing preparation.

Measurement results of the enclosure ratio of chemical, the average vesicular particle size and particle size distribution (which is the percentage of particles of 1 μm or more) are shown in Table 2.

Example 5

Dipalmitoylphosphatidylcholine (DPPC) of 300 mg, 100 mg of PEG-phospholipid (SUNBRIGHT DSPE-020CN) and 10 g of an aqueous solution of Iopamidol (iodine content: 250 mg/ml) were mixed and dispersed over a period of 5 min. using a magnetic stirrer (a nearly cylindrical stirring rod of 15 mm length and 5 mm diameter) at a rate of ca. 1200 rpm to obtain a suspension. The suspension was added into a stainless steel pressure vessel, and after 13 g of liquefied carbon dioxide was added thereto, the interior of the vessel was made to a temperature of 60° C. and a pressure of 120 kg/cm$^2$ to bring the carbon dioxide to the supercritical state and such a state was further maintained for 5 min. Thereafter, the pressure within the pressure vessel was reduced to ca. 10 kg/cm$^2$ to discharge carbon dioxide. Employing the pressure within the vessel, a dispersion was discharged from the vessel and recovered to obtain a liposome dispersion containing Iopamidol. Further, the thus obtained dispersion was subjected to pressure filtration using a 0.45 μm cellulose type filter. After completion of filtration, the liposome dispersion was put into a vial and subjected to autoclave sterilization at 121° C. for 20 min. to obtain a liposome-containing preparation.

Measurement results of the enclosure ratio of chemical, the average vesicular particle size and particle size distribution (which is the percentage of particles of 1 μm or more) are shown in Table 2.

Example 6

Dipalmitoylphosphatidylcholine (DPPC) of 300 mg, 40 mg of cholesterol HP (afore-mentioned), 50 mg of dipalmotoylphsphatudylglycerol (COATSOME MG-6060LS, product by NIPPON OIL &FATS CO., LTD.) as a glycerol lipid and 10 g of an aqueous solution of Iopamidol (iodine content: 250 mg/ml) were mixed and dispersed over a period of 3 min. using a compact homogenizer (ULTRATALAX, trade name, produced by IKA Japan Corp.) at a rate of 6000 rpm to obtain a suspension. The suspension was added into a stainless steel pressure vessel, and after 13 g of liquefied carbon dioxide was added thereto, the interior of the vessel was made to a temperature of 55° C. and a pressure of 120 kg/cm$^2$ to bring the carbon dioxide to the supercritical state and such a state was further maintained for 5 min. Thereafter, the pressure within the pressure vessel was reduced to ca. 10 kg/cm$^2$ to discharge carbon dioxide. Employing the pressure within the vessel, a dispersion was discharged from the vessel and recovered to obtain a liposome dispersion containing Iopamidol. Further, the thus obtained dispersion was subjected to pressure filtration using a 1 μm cellulose type filter. After completion of filtration, the liposome dispersion was put into a vial and subjected to autoclave sterilization at 121° C. for 20 min. to obtain a liposome-containing preparation.

Measurement results of the enclosure ratio of chemical, the average vesicular particle size and particle size distribution (which is the percentage of particles of 1 μm or more) are shown in Table 2.

Example 7

Dipalmitoylphosphatidylcholine (DPPC) of 300 mg, 40 mg of cholesterol HP (afore-mentioned), 100 mg of PEG-phospholipid (SUNBRIGHT DSPE-020CN) and an aqueous solution of 10 mg of doxorubicin dissolved in 10 ml of physiological saline were mixed and dispersed over a period of 3 min. using a compact homogenizer (ULTRATALAX, trade name, produced by IKA Japan Corp.) at a rate of 6000 rpm to obtain a suspension. The suspension was added into a stainless steel pressure vessel, and after 13 g of liquefied carbon dioxide was added thereto, the interior of the vessel was made to a temperature of 60° C. and a pressure of 120 kg/cm$^2$ to bring the carbon dioxide to the supercritical state and such a state was further maintained for 5 min. Thereafter, the pressure within the pressure vessel was reduced to ca. 10 kg/cm$^2$ to discharge carbon dioxide. Employing the pressure within the vessel, a dispersion was discharged from the vessel and recovered to obtain a liposome dispersion containing doxorubicin. Further, the thus obtained dispersion was subjected to pressure filtration using a 0.45 μm cellulose type filter. After completion of filtration, the liposome dispersion was put into a vial and subjected to autoclave sterilization at 121° C. for 20 min. to obtain a liposome-containing preparation.

Measurement results of the enclosure ratio of chemical, the average vesicular particle size and particle size distribution (which is the percentage of particles of 1 μm or more) are shown in Table 2.

Example 8

Dipalmitoylphosphatidylcholine (DPPC) of 300 mg, 60 mg of cholesterol HP (afore-mentioned), 20 mg of dipalmotoylphsphatudylglycerol (COATSOME MG-6060LS, product by NIPPON OIL &FATS CO., LTD.) as a glycerol lipid and 10 g of an aqueous solution of Iopalmidol (iodine content: 250 mg/ml) were mixed and dispersed over a period of 3 min. using a magnetic stirrer (a nearly cylindrical stirring rod of 15 mm length and 5 mm diameter) at a rate of ca. 1200 rpm while being exposed to ultrasonics to obtain a suspension. The suspension was added into a stainless steel pressure vessel, and after 13 g of liquefied carbon dioxide was added thereto, the interior of the vessel was made to a temperature of 55° C. and a pressure of 120 kg/cm$^2$ to bring the carbon dioxide to the supercritical state and such a state was further maintained for 20 min. Thereafter, the pressure within the pressure vessel was reduced to ca. 10 kg/cm$^2$ to discharge carbon dioxide. Employing the pressure within the vessel, a dispersion was discharged from the vessel and recovered to obtain a liposome dispersion containing Iopamidol. Further, the thus obtained dispersion was subjected to pressure filtration using a 0.45 μm cellulose type filter. After completion of filtration, the liposome dispersion was put into a vial and subjected to autoclave sterilization at 121° C. for 20 min. to obtain a liposome-containing preparation.

Measurement results of the enclosure ratio of chemical, the average vesicular particle size and particle size distribution (which is the percentage of particles of 1 μm or more) are shown in Table 2.

TABLE 2

|  | Order of Addition*1 | Mixing*2 | Enclosure Ratio (%) | Average Particle Size (μm) | Particle Size Distribution (%) |
|---|---|---|---|---|---|
| Example 4 | A | a | 17 | 0.31 | <5*3 |
| Example 5 | A | b | 16 | 0.35 | 9 |
| Example 6 | A | a | 17 | 0.26 | 8 |
| Example 7 | A | a | 19 | 0.29 | <5 |
| Example 8 | A | c + a | 17 | 0.22 | <5 |

*1A: membrane constituent → chemical → CO2
B: membrane constituent → CO$_2$ → chemical
*2a: homogenizer; b: stirring rod; c: ultrasonics
*3less than 5

What is claimed is:

1. A method of manufacturing a liposome-containing preparation comprising mixing a supercritical carbon dioxide, one or more liposome membrane constituents including a phospholipid exhibiting a phase transition temperature and a water-soluble chemical, and the method comprises the steps of:
    (a) mixing one or more liposome membrane constituents and liquefied carbon dioxide in a pressure vessel,
    (b) increasing a pressure within the vessel with heating at a temperature of 32 to 55° C. to bring the carbon dioxide to a supercritical state,
    (c) supplying an aqueous solution of the water-soluble chemical to a mixture of the liposome membrane constituent and the supercritical carbon dioxide with stirring to form a mixed solution, and
    (d) decreasing the pressure within the vessel to discharge the carbon dioxide from the mixed solution to form an aqueous dispersion of liposomes enclosing the water-soluble chemical
    wherein the liposome membrane constituents include a compound containing a polyethylene glycol group, and in step (c), stirring is subjected to strong agitation satisfying the following requirement:

$$C = N \times V^{-0.15}$$

wherein C is a number of revolutions per minute (rpm), V is a volume (L) of a mixed solution and N is 300 to 3000.

2. The method of claim 1, wherein the phase transition temperature of the phospholipid is within the range of 22 to 60° C.

3. The method of claim 1, wherein the phospholipid exhibiting a phase transition temperature is at least one selected from the group of hydrogenated soybean lecithin, hydrogenated phosphatidylcholine and distearoylphosphatidylcholine.

4. The method of claim 1, wherein the phospholipid exhibiting a phase transition temperature is dimyristoylphosphatidylcholine or dipalmitoylphosphatidylcholine.

5. The method of claim 1, wherein the water-soluble chemical is a contrast medium compound or an anticancer compound.

6. The method of claim 5, wherein, the water soluble compound is the contrast medium compound which is a water-soluble iodine compound.

7. The method of claim 1, wherein in step (b), the temperature is 32 to 50° C.

8. The method of claim 1, wherein in step (c), the stirring is subjected to strong agitation at a rate of 400 to 4,000 rpm.

9. The method of claim 1, wherein the method further comprises (e) subjecting the aqueous dispersion of liposomes to filtration using a membrane filter having a pore size of 0.1 to 1.0 μm.

10. The method of claim 1, wherein the compound containing a polyethylene glycol group is a phospholipid containing a polyethylene glycol group or a cholesterol containing a polyethylene glycol group.

11. The method of claim 1, wherein a weight ratio of chemical included in vesicles to lipid forming vesicular membrane is 1 to 8.

* * * * *